US00PP28709P2

(12) United States Plant Patent
Hanes

(10) Patent No.: US PP28,709 P2
(45) Date of Patent: Nov. 28, 2017

(54) ***PELARGONIUM* PLANT NAMED 'PEQZ0015'**

(50) Latin Name: *Pelargonium interspecific*
Varietal Denomination: PEQZ0015

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,976

(22) Filed: Jul. 21, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

*Primary Examiner* — Annette Para
(74) *Attorney, Agent, or Firm* — Dale Skalla

(57) ABSTRACT

A new *Pelargonium* plant named 'PEQZ0015' particularly distinguished by its dark red, semi double, inflorescences held above the medium dark green foliage. The variety is very heat and drought tolerant with continuous color through the extreme summer heat, and displays exceptional oedema tolerance on a vigorous plant.

1 Drawing Sheet

Figure 1:
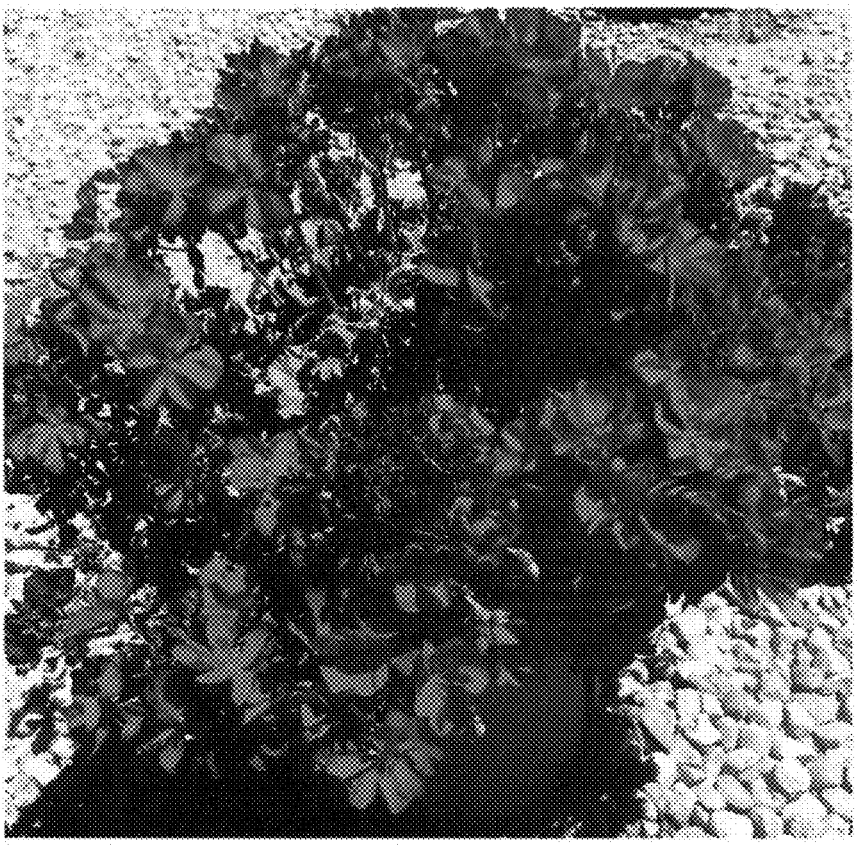

Latin name of the genus and species of the plant claimed: *Pelargonium interspecific.*

Varietal denomination: 'PEQZ0015'.

BACKGROUND OF THE NEW PLANT

The present invention comprises a new *Pelargonium*, botanically known as *Pelargonium interspecific*, and hereinafter referred to by the variety name 'PEQZ0015'.

'PEQZ0015' is a product of a planned breeding program. The new cultivar 'PEQZ0015' has dark red, semi double, inflorescences held above the medium dark green foliage. The variety is very heat and drought tolerant with continuous color through the extreme summer heat and displays exceptional oedema tolerance on a vigorous plant.

'PEQZ0015' originates from a hybridization in a controlled breeding program made in June 2011 in a greenhouse in Guatemala. The female parent was an unpatented, proprietary plant of *P. interspecific* parentage, identified as '11027-3' which is a compact, well zoned plant, with cherry rose colored flowers and shorter flower stems when compared to 'PEQZ0015'.

The male parent of 'PEQZ0015' was an unpatented, proprietary plant of *P. interspecific* parentage, identified as '10902-4' with hot rose colored flowers and a more open plant habit when compared to 'PEQZ0015'. The resultant seed was sown in July 2012.

Both the female and male parents of 'PEQZ0015' are direct descendants of the commercial geranium variety "Calliope Dark Red" also known as 'Amri Trared', U.S. Plant Pat. No. 20,245, and this is the source of the color pigment genes giving the dark red color of 'PEQZ0015'.

'PEQZ0015' was selected as one flowering plant within the progeny of the stated cross in October 2012 in a greenhouse in Gilroy, Calif.

The first act of asexual reproduction of 'PEQZ0015' was accomplished when vegetative cuttings were propagated from the initial selection in the December 2012 in a greenhouse in Gilroy, Calif.

BRIEF SUMMARY OF INVENTION

Horticultural examination of plants grown from cuttings of the plant initiated on Jun. 24, 2016 in Gilroy, Calif., and continuing thereafter, has demonstrated that the combination of characteristics as herein disclosed for 'PEQZ0015' are firmly fixed and are retained through successive generations of asexual reproduction.

'PEQZ0015' has not been observed under all possible environmental conditions. The phenotype may vary significantly with variations in environment such as temperature, light intensity, and day length.

A Plant Breeder's Right for this cultivar has not yet been filed. 'PEQZ0015' has not been made publicly available prior to the effective filing date of this application, notwithstanding any disclosure that may have been made less than one year prior to the effective filing date of this application by the inventor or another who obtained 'PEQZ0015' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 2:
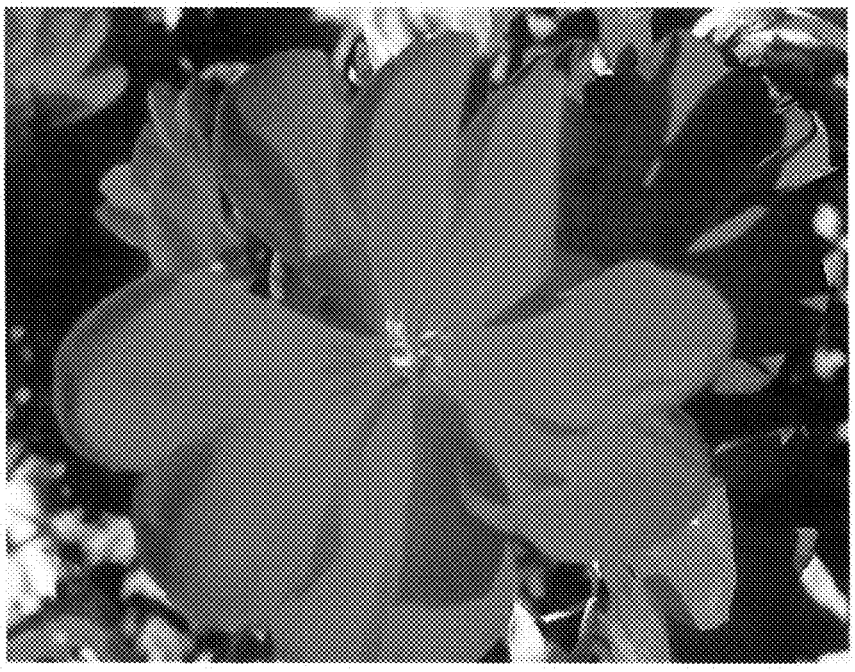

The accompanying photographic drawings show typical flower and foliage characteristics of 'PEQZ0015' with colors being as true as possible with an illustration of this type. The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. on Jun. 24, 2016 under natural light. These plants were approximately 18 weeks old and were grown in a 14 inch pot in a greenhouse trial. The plants shown in the photographs were about 18 weeks old growing in 14 inch pots in a container field. The photographs were taken on Jul. 7, 2016.

Color references are made to The Royal Horticultural Society Colour Chart (R.H.S.) 2001.

TABLE 1

DIFFERENCES BETWEEN THE NEW VARIETY 'PEQZ0015' AND A MOST SIMILAR VARIETY

| | 'PEQZ0015' | 'Amri Trared' (U.S. Plant Pat. No. 20,245) |
|---|---|---|
| Floret size: | 4.8-5.0 cm | 5.0-5.5 cm |
| Floret petal color: | Dark red | Dark red |
| Umbel diameter size: | 9.5-10.5 cm | 11-14 cm |
| Peduncle length: | 11.5-12.0 cm | 11.5-15.0 cm |

Plant:

*Form, growth and habit.*—Upright, outwardly spreading and rounded growth habit, heat and drought tolerant with continuous color through the most extreme summer heat, oedema tolerance, well-branched plant habit.

*Plant height.*—18-19 cm.

*Plant height (inflorescence included).*—23.5-24 cm.

*Plant width.*—35-37 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS 155B.

Foliage:

*Immature leaf, color upper surface.*—RHS 146B.

*Immature leaf, lower surface.*—RHS 137C.

*Mature leaf, color upper surface.*—RHS 137B.

*Mature leaf, color lower surface.*—RHS 137C.

*Length.*—4.8-5.5 cm.

*Width.*—8.0-8.5 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137A becoming indistinct.

*Color of veins, lower surface.*—RHS 138B becoming indistinct.

*Pattern of veining.*—Palmate.

*Petiole color.*—RHS 137C.

*Petiole length.*—7.5-7.8 cm.

*Diameter of petiole.*—0.25-0.3 cm.

*Texture.*—Pilose, hirsute, glandular hairs.

Stem:

*Quantity of branches.*—8-10.

*Color of stem.*—RHS 145A.

*Length of stem.*—11.5-13 cm.

*Diameter.*—0.7 cm.

*Length of internodes.*—3.2-3.5 cm.

*Texture.*—Sparsely hirsute, pilose, glandular hairs.

Peduncle:

*Color of peduncle.*—RHS N144A with red.

*Length of peduncle.*—11.5-12 cm.

*Peduncle diameter.*—0.3-0.35 cm.

*Texture.*—Hirsute, glandular hairs.

Pedicel:

*Color of pedicel.*—RHS 187C.

*Length of pedicel.*—2.5-2.7 cm.

*Diameter of pedicel.*—0.15-0.2 cm.

*Texture.*—Sparsely pilose, glandular hairs.

Bud (just before opening):

*Color.*—RHS 187A.

*Length.*—1.4 cm.

*Width.*—0.7-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12, with 15 immature umbels in various stages.

*Fragrance.*—None.

*Umbel diameter.*—9.5-10.5 cm.

*Umbel depth.*—4.8-5.0 cm.

Corolla:

*Form.*—Semi-double.

*Number of petals.*—9-10.

*Diameter of flower.*—4.8-5.0 cm.

*Depth of flower.*—2-2.3 cm.

*Color upper petals, upper surface.*—RHS 53A.

*Color upper petals, lower surface.*—Closest to RHS 46A.

*Length of upper petals.*—2.5-2.7 cm.

*Width of upper petals.*—1.7-2.0 cm.

*Color lower petals, upper surface.*—RHS 53A.

*Color lower petals, lower surface.*—RHS 46A.

*Length of lower petals.*—2.5 cm.

*Width of lower petals.*—1.8 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144B with anthocyanin.

*Length of sepals.*—1.2 cm.

*Width of sepals.*—0.4-0.5 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.9 cm.

*Style color.*—RHS 53D.

*Style length.*—0.5 cm.

*Stigma color.*—RHS 53D.

*Ovary color.*—RHS 145A.

*Ovary length.*—0.5-0.6 cm.

*Ovary diameter.*—0.2 cm.

Androecium:

*Number of stamens.*—6-7.

*Color of filaments.*—RHS N57B.

*Length filaments.*—0.7 cm.

*Anther color.*—RHS 53A.

*Length of anthers.*—0.2 cm.

*Color of pollen*.—RHS 25B.

*Pollen amount*.—Normal.

*Fertility/seed set*.—Has not been determined to date.

*Disease/pest resistance*.—Has not been determined to date.

What is claimed is:

1. A new and distinct variety of *Pelargonium* plant named 'PEQZ0015' substantially as illustrated and described herein.

* * * * *